United States Patent
Deavenport et al.

(10) Patent No.: US 9,493,398 B2
(45) Date of Patent: Nov. 15, 2016

(54) ETHER DYE FIXATIVE AGENTS AND METHODS

(71) Applicant: Dow Global Technologies LLC, Midland, MI (US)

(72) Inventors: Joseph L. Deavenport, Lake Jackson, TX (US); Timothy S. De Vries, Midland, MI (US)

(73) Assignee: Dow Global Technologies LLC

(*) Notice: Subject to any disclaimer, the term of this patent is extended or adjusted under 35 U.S.C. 154(b) by 0 days.

(21) Appl. No.: 14/422,725

(22) PCT Filed: Sep. 18, 2013

(86) PCT No.: PCT/US2013/060275
§ 371 (c)(1),
(2) Date: Feb. 20, 2015

(87) PCT Pub. No.: WO2014/047099
PCT Pub. Date: Mar. 27, 2014

(65) Prior Publication Data
US 2015/0210627 A1    Jul. 30, 2015

Related U.S. Application Data

(60) Provisional application No. 61/704,062, filed on Sep. 21, 2012.

(51) Int. Cl.
| | |
|---|---|
| *C11D 3/26* | (2006.01) |
| *C11D 3/40* | (2006.01) |
| *C07C 217/08* | (2006.01) |
| *D06P 5/00* | (2006.01) |
| *D06P 5/22* | (2006.01) |
| *D06P 1/66* | (2006.01) |

(52) U.S. Cl.
CPC .............. *C07C 217/08* (2013.01); *D06P 1/66* (2013.01); *D06P 5/002* (2013.01); *D06P 5/225* (2013.01)

(58) Field of Classification Search
CPC ..... C11D 3/0021; C11D 3/26; C11D 3/2068; C11D 3/3927; C11D 3/40; C11D 7/263; C11D 9/444; C11D 11/0017
See application file for complete search history.

(56) References Cited

U.S. PATENT DOCUMENTS

| | | |
|---|---|---|
| 2,261,294 A | 11/1941 | Schlack |
| 3,547,986 A | 12/1970 | Falcone et al. |
| 4,506,081 A | 3/1985 | Fenyes et al. |
| 4,778,813 A | 10/1988 | Fenyes et al. |
| 5,330,541 A | 7/1994 | Hall et al. |
| 5,489,313 A | 2/1996 | Hall et al. |

FOREIGN PATENT DOCUMENTS

| | | |
|---|---|---|
| GB | 514861 | 11/1939 |
| GB | 2160538 | * 12/1985 |

OTHER PUBLICATIONS

Sharif, et al., Chinese Journal of Chemistry, "Synthesis and Spectroscopic Characterisation of 2,3-Epoxy/3-Chloro-2-hydroxy Propyl Derivatives of Quaternary Ammonium Salts: Useful Cationic Fixing Agents", 2008, vol. 26, pp. 553-559.

* cited by examiner

*Primary Examiner* — Charles Boyer

(57) ABSTRACT

Described are dye fixative agents, comprising an ether compound, including salts, of Formula I: wherein, $R_1$ is, independently at each occurrence, C1-C6 alkyl; $R_2$ and $R_3$, are, independently at each occurrence, optionally substituted C6 alkyl; and X is, independently at each occurrence, CI, Br, or I.

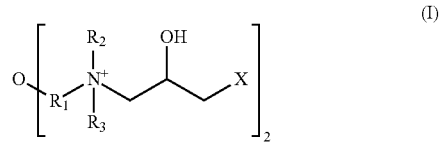

9 Claims, No Drawings

ETHER DYE FIXATIVE AGENTS AND METHODS

CROSS REFERENCE TO RELATED APPLICATION(S)

This application is a 35 USC §371 national phase filing of PCT/US2013/060275 filed Sep. 18, 2013, which claims priority from U.S. Provisional Patent Application No. 61/704,062, filed Sep. 21, 2012, which is incorporated herein by reference in its entirety.

FIELD

The following disclosure relates generally to textile treatment methods, and more particularly to dye fixative agents.

BACKGROUND

Creating "cationic cotton" by introducing a positive charge to a cotton fabric or textile for increased dye uptake is well known. One of the most common methods is to use epoxy based ammonium compounds, such as 3-chloro-2-hydroxypropyltrimethylammonium chloride (commercially available under the tradename CR-2000), to add a charge to the cotton's cellulose polymer backbone.

However, there are unmet needs in the art to increase relative dye uptake, generate less waste in the treatment of cotton fabric, and provide a lower cost to treat than conventional additives.

DETAILED DESCRIPTION

In one embodiment, the present invention includes a dye fixative agent, comprising an ether compound, including salts, of Formula I:

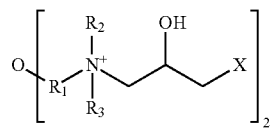

(I)

wherein,
$R_1$ is, independently at each occurrence, C1-C6 alkyl;
$R_2$ and $R_3$, are, independently at each occurrence, optionally substituted C1-C6 alkyl; and
X is, independently at each occurrence, Cl, Br, or I.

"Dye fixative agent" means an agent for introducing a positive charge to a cotton fabric or textile for increased dye uptake, as dye particles are anionic. For comparison, CR-2000 has a reaction efficiency of greater than 7% (see Example 3), and accordingly, compounds of Formula I having at least equal performance are dye fixative agents.

"Optionally substituted" means that the groups in question are either unsubstituted or substituted with one or more groups, radicals or moieties, selected from halogen, hydroxy, amino or carboxy. "Amino" is intended to include amino further substituted with C1-C3alkyl, preferably trimethylamino ($—N^+(CH_3)_3$). When the groups in question are substituted with more than one substituent, the substituents may be the same or different. In one embodiment, the optional substituent is one or more hydroxy groups.

"Alkyl" means a saturated monovalent linear or branched aliphatic hydrocarbon radical. Representative examples include, but are not limited to methyl, ethyl, propyl, isopropyl, butyl, isobutyl, tert-butyl, sec-butyl, pentyl, isopentyl, neopentyl, hexyl, isohexyl, and the like.

Salts means that a counter-ion is present, preferably halogen, more preferably Cl⁻.

In a preferred embodiment, X is Cl.

In one embodiment, $R_2$ and $R_3$ are the same in at least two occurrences. In one embodiment, $R_2$ and $R_3$ are not the same in at least two occurrences. In one embodiment, $R_2$ and $R_3$ are the same in all four occurrences.

In one embodiment, the ether compound of Formula I is symmetrical. In other words, both $R_1$ occurrences are the same, both $R_2$ occurrences are the same, both $R_3$ occurrences are the same, and both X occurrences are the same. A non-limiting example of this embodiment is the reaction products of Bis[2-(N,N-dimethylamino)ethyl]ether and epichlorohydrin:

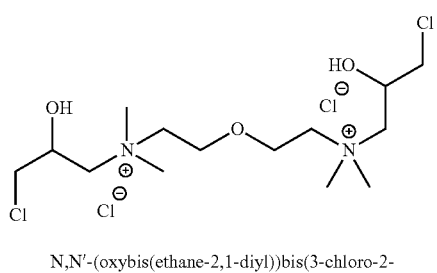

N,N'-(oxybis(ethane-2,1-diyl))bis(3-chloro-2-hydroxy-N,N-dimethylpropan-1-aminium) chloride In one embodiment, the ether compound of Formula I is asymmetrical. In other words, at least one of the following: the two $R_1$ occurrences are not the same, the two $R_2$ occurrences are not the same, or the two $R_3$ occurrences are not the same. In one embodiment, when $R_1$ is —$CH_2CH_2$— at its first occurrence, it is other than —$CH_2CH_2$— at its second occurrence. A non-limiting example of this embodiment is reaction of epichlorohydrin with 3-(2-(dimethylamino)ethoxy)-N—N-dimethylpropan-1-amine to produce 3-chloro-N-(3-(2-((3-chloro-2-hydroxypropyl)dimethylammonio)ethoxy)propyl)-2-hydroxy-N,N-dimethylpropan-1-aminium chloride.

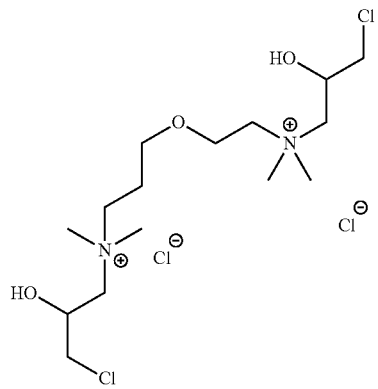

3-chloro-N-(3-(2-((3-chloro-2-hydroxypropyl)dimethylammonio)ethoxy)-propyl)-2-hydroxy-N,N-dimethylpropan-1-aminium chloride Another non-limiting example of this embodiment is reaction of epichlorohydrin with 2,2'-oxybis(n-ethyl-N-methylethanamine) to produce N,N'-(oxybis(ethane-2,1-diyl))bis(3-chloro-N-ethyl-2-hydroxy-N-methylpropan-1-aminium)

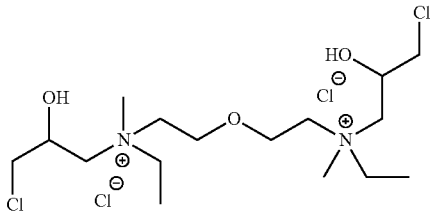

N,N'-(oxybis(ethane-2,1-diyl))bis(3-chloro-N-ethyl-2-hydroxy-N-methylpropan-1-aminium)

Another non-limiting example of this embodiment is reaction of epichlorohydrin with N-(2-(2-(ethyl(methyl)amino)ethoxy)ethyl)-N-methylpropan-1-amine to produce 3-chloro-N-(2-(2-((3-chloro-2-hydroxypropyl)(ethyl)(methyl)ammonio)ethoxy)ethyl)-2-hydroxy-N-methyl-N-propylpropan-1-aminium chloride.

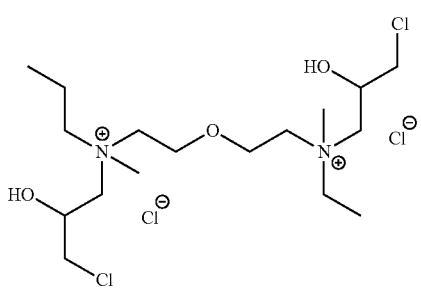

3-chloro-N-(2-(2-((3-chloro-2-hydroxypropyl)(ethyl)(methyl)ammonio)ethoxy)-ethyl)-2-hydroxy-N-methyl-N-propylpropan-1-aminium chloride Another non-limiting example of this embodiment is reaction of epichlorohydrin with 1-(2-(dimethylamino)ethoxy)-N,N,2-trimethylpropan-2-amine to produce 3-chloro-N-(2-(2-((3-chloro-2-hydroxypropyl)dimethylammonio)-methylpropoxy)ethyl)-2-hydroxy-N,N-dimethylpropan-1-aminium chloride

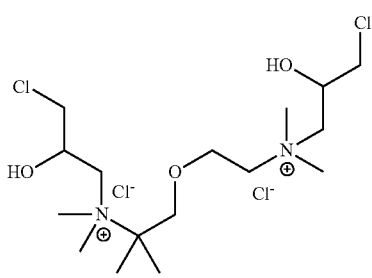

3-chloro-N-(2-(2-((3-chloro-2-hydroxypropyl)dimethylammonio)-2-methylpropoxy)ethyl)-2-hydroxy-N,N-dimethylpropan-1-aminium chloride In use, the present dye fixative agents find use in methods of treating fabric, comprising applying to the fabric the dye fixative agent.

EXAMPLES

The following examples are illustrative of some embodiments of the present invention.

Example 1

Bis[2-(N,N-dimethylamino)ethyl]ether was reacted with Epichlorohydrin. The diamine and distilled water are mixed (10.84 g diamine (0.07 mole)/23.12 g water), and pH adjusted to 8.5 with concentrated hydrochloric acid. The temperature is adjusted to 25° C., and over a period of 60 minutes 99.9% Epichlorohydrin (20.84 g (0.22 mole)) is added. The temperature is held at 25° C. for 2 hours, then raised to 50° C. for 2 hours. The pH is lowered to <2.0 with concentrated hydrochloric acid and the temperature increased to 70° C. for 1 hour. The reaction is then cooled, and the pH adjusted to 4-6 with 50% NaOH solution after the temperature falls below 50° C. An extraction is performed with methylene chloride seven times (1vol:1vol), then the residual methylene chloride is removed conventionally. The active solids of Batch 1 was 39.4%.
$^{13}$C NMR of the product confirmed the formation of N,N'-(oxybis(ethane-2,1-diyl))bis(3-chloro-2-hydroxy-N,N-dimethylpropan-1-aminium) chloride, henceforth referred to as Batch 1.

Example 2

For color analysis, cotton samples were treated with a composition substantially according to Example 1 (Batch 1) and a comparative (CR-2000 available from The Dow Chemical Company).

The treatment levels were approximately the same on a molar basis. Cotton was reacted with each compound in an approximately equimolar amount compared to a 50 g/L CR-2000 treatment using an Ahiba IR dyeing machine. An equimolar amount of sodium hydroxide was used relative to the quat compound and an additional catalytic amount of 0.24 mole NaOH per mole of cotton (based on 162 g/mole monomer mw). The reactions with cotton were done at 70° C. for one hour with an 8:1 liquor ratio. The treated samples were dipped in a beaker of water, a beaker of 1 g/L acetic acid and a final beaker of water before being dried in a 50° C. oven. The amount of sodium hydroxide used was enough to epoxidize the chlorohydrin present and an additional amount as a catalyst to activate some of the hydroxyl groups in the cellulose.

The treated cotton from each candidate was analyzed for percent nitrogen using a LECO® Nitrogen Analyzer and method (LECO Form No. 203-821-140, "Carbon, and Nitrogen in Textile, Fabric, and Cotton", 08/10 rev 2). The theoretical degree of substitution ("Theo DS") is the moles of reagent divided by the moles of anhydroglucose monomer units in the cotton. The Theo DS for CR-2000 was 0.226, and the Theo DS for Batch 1 was 0.223. The percent nitrogen ("% N") was determined by analyzing a sample on the LECO® Nitrogen Analyzer. The % N for CR-2000 was 0.135, and % N for Batch 1 was 0.242.

The treated samples were then dyed with 1.7 g/L of Acid Red 1. The treated cotton samples were dyed in the Ahiba IR dyeing machine at 80° C. for 20 minutes with a ramp time of 4° C./minute. The dyed cotton was rinsed with tap water a total of three times. The first rinse is at 30° C. for 10 minutes followed by two hot rinses at 80° C. for 10 minutes each. The samples were dried overnight in a 50° C. oven. The dyed samples were analyzed by a Hunter Lab MiniScan EZ Spectrophotometer (Model 4500 L) to determine the L*, a*, and b*. The color values for each sample are shown in TABLE 1:

TABLE 1

|  | L* | a* | b* |
|---|---|---|---|
| (Comparative) CR-2000 treated | 39.58 | 57.89 | 24.25 |
| Batch 1 treated | 34.54 | 53.61 | 28.58 |

Batch 1 had a deeper shade of red compared to the CR-2000 as indicated by the lower L* value which indicates the lightness of the color (0 is black and 100 is white).

Example 2

For dye reaction efficiency analysis, cotton samples were treated with the compositions described in TABLE 2:

TABLE 2

| | Structure | % N | Actual DS | Theo DS | RE |
|---|---|---|---|---|---|
| Batch 1 | 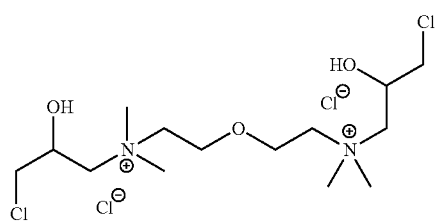 [SMILES: C[N+](C)(CCOCC[N+](C)(C)CC(O)CCl)CC(O)CCl ; [Cl-] ; [Cl-]] | 0.140 | 0.0068 | 0.044 | 15.3% |
| Comparative CF-2000 | 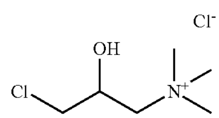 | 0.058 | 0.0040 | 0.046 | 8.6% |
| Comparative $N^1,N^2$-bis(3-chloro-2-hydroxypropyl)-$N^1,N^1,N^2,N^2$-tetramethylethane-1,3-diaminium chloride | 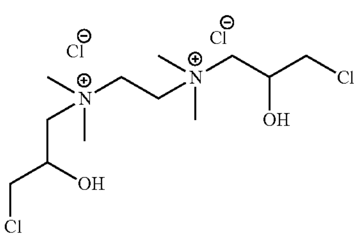 [SMILES: [Cl-] ; [Cl-] ; C[N+](C)(CC[N+](C)(C)CC(O)CCl)CC(O)CCl] | 0.078 | 0.0031 | 0.045 | 7.0% |
| Comparative 3-chloro-2-hydroxy-N-(2-(2-hydroxyethoxy)ethyl)-N,N-dimethylpropan-1-aminium chloride | 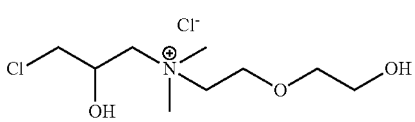 | 0.061 | 0.0043 | 0.045 | 9.7% |

Amount of each reagent used in Table 2 was adjusted to be equivalent to about 0.045 mole per mole of cotton (theoretical DS). The treating protocol substantially according to Example 2 was used, including dye. What is surprising is that while the comparative ether and comparative quaternary amines (mono-amine or di-amine) worked fairly equivalently, Batch 1 (an ether coupling two amines) worked dramatically better.

"RE" means reaction efficiency and is calculated by the dividing the actual degree of substitution by the theoretical degree of substitution. Actual DS means actual degree of substitution and is the mole of reagent reacted onto the moles of cotton. Theoretical DS means theoretical degree of substitution and is the mole of reagent attempted to react onto the moles of cotton.

The invention claimed is:

1. A textile comprising:
   a fabric;
   a dye; and
   an ether compound, including salts, of Formula I:

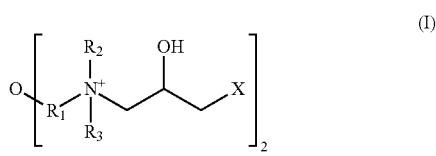

wherein, $R_1$ is, independently at each occurrence, C1-C6 alkyl;

$R_2$ and $R_3$, are, independently at each occurrence, optionally substituted C1-C6 alkyl; and X is, independently at each occurrence, Cl, Br, or I.

2. The textile of claim 1, with the proviso that, when $R_1$ is —CH2CH2- at its first occurrence, it is other than —CH2CH2- at its second occurrence.

3. The textile of claim 1, wherein $R_2$ and $R_3$ are the same in at least two occurrences.

4. The textile of claim 1, wherein $R_2$ and $R_3$ are the same in all four occurrences.

5. The textile of claim 1, wherein $R_2$ and $R_3$ are not the same in at least two occurrences.

6. The textile of claim 1, wherein the ether compound of Formula I is symmetrical.

7. The textile of claim 1, wherein the ether compound of Formula I is asymmetrical.

8. The textile of claim 1, wherein X is Cl.

9. A method of treating a textile, comprising applying to the fabric the dye fixative agent and dye of claim 1.

* * * * *